Sept. 22, 1953 R. L. BYRUM Plant Pat. 1,217
ROSE PLANT
Filed Oct. 3, 1952
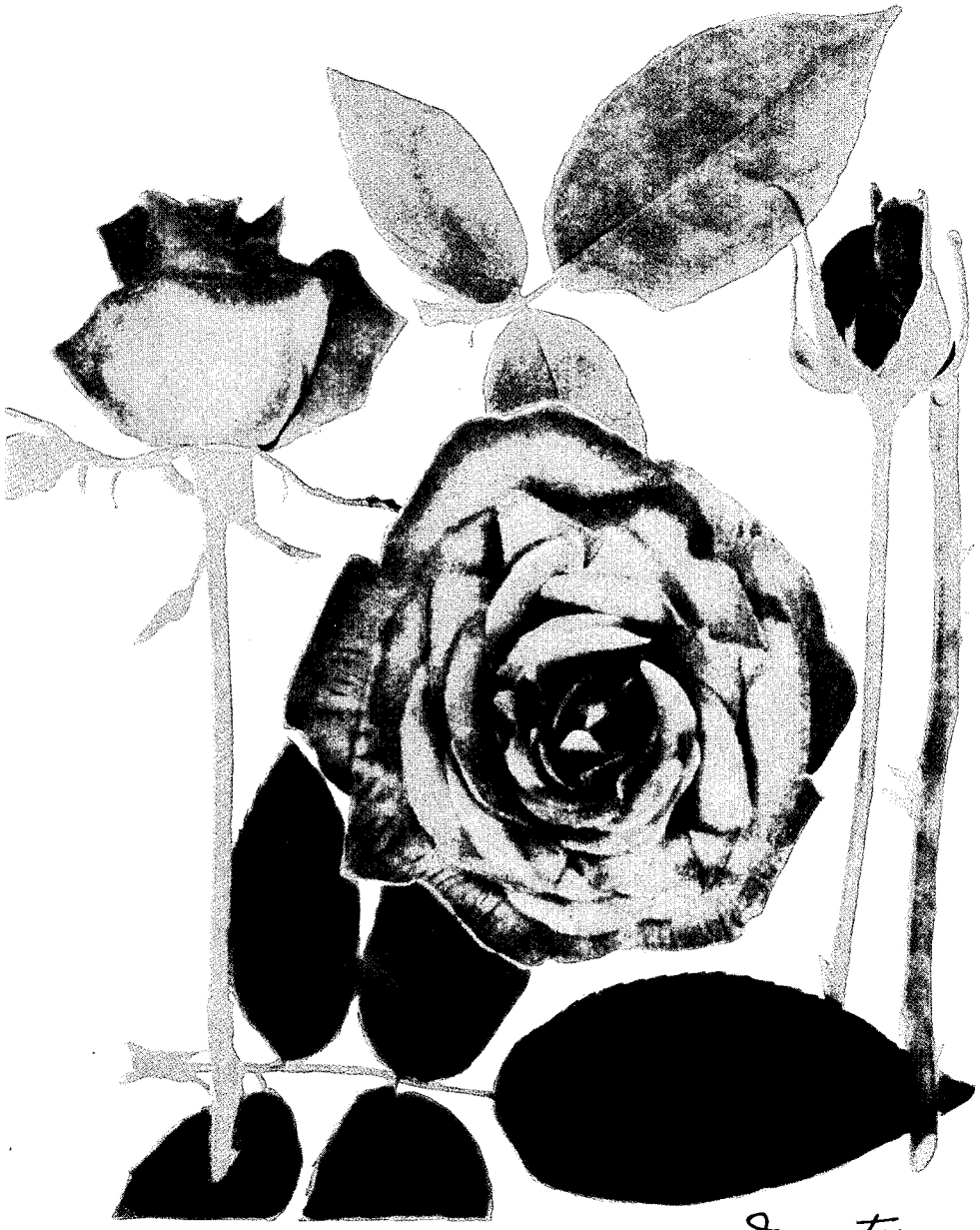
Inventor.
R. L. Byrum
By: Robert Robb
Attorneys.

Patented Sept. 22, 1953

Plant Pat. 1,217

UNITED STATES PATENT OFFICE 1,217

ROSE PLANT

Roy L. Byrum, Richmond, Ind., assignor to Joseph H. Hill Company, Richmond, Ind., a corporation of Indiana Application October 3, 1952, Serial No. 313,096

1 Claim. (Cl. 47—61)

The present invention relates to a new and distinct variety of rose plant which was discovered by me as a sport of an unnamed and unpatented seedling designated in my experimental and test records by the identification #45/35R.

The seedling parent of the present variety was originated by crossing the unpatented variety known as "Captivator," which is a sport of "Better Times" (Plant Patent No. 23), but the flowers of which have a pink color comparable to "Peter's Briarcliff" (unpatented), with the variety known as "Red Delicious" (Plant Patent No. 620). In making the cross from which the parent seedling of the present variety was produced, the variety "Captivator" was employed as the seed parent, and the variety "Red Delicious" as the pollen parent, which cross had for its objective to improve the pollen parent in stem strength and to otherwise obtain a generally improved red rose variety.

At the time of the discovery of my new sport, a block of plants of the parent variety #45/35R were being grown in a greenhouse under my direction and supervision and owned and controlled by my assignee-employer, for test and observation purposes. My attention was attracted to one of these test plants by reason of the fact that one cane having a very much stronger growth was produced than the other canes on the same plant. I thereupon promptly budded in eyes of the sport cane into canes of another variety and found that these budded eyes produced canes with the same strong-growing characteristic. Additional propagations were made by grafting and own-rooting the new sport, and in each instance, the same strong-growing characteristic was found to be fixed and established, together with the fact that the growth of the new variety was more uniform, the colors of the flowers produced thereby were unusually uniform throughout the different stages of development from tight bud to fully open flower, the Rose Red color of each flower was unusually uniform throughout each bloom, and the flowers were unusually resistant to burn, fading and other effects of the sun. In addition to these characteristics, my new variety has been found to have exceptional depth, intensity and luminosity of the Rose Red general color tonality of its flowers. The flowers have a strong and distinctive tea fragrance and are borne on bushes which have a compact habit of growth. This unique combination of characteristics definitely established my new sport as a new variety, and all of the foregoing characteristics and distinctions have been proved as coming true to form and are transmitted through succeeding propagations by budding, grafting and own-rooting, as performed by me at Richmond, Indiana.

The accompanying drawing shows specimens of the flowers, foliage and stems of my new variety, with the flowers and foliage in different stages of development.

The following is a detailed description of my new variety, with color terminology in accordance with Koster's Color Guide (abbreviated as "Koster") and Robert F. Wilson's Horticultural Colour Chart (abbreviated as "Wilson"), except where general color terms of ordinary dictionary significance are obvious:

Type: Hardy; sport; bush.

Class: Hybrid tea.

Parentage: Sport of unnamed seedling #45/35R originated as a cross of "Captivator" × "Red Delicious."

Propagation: Holds its distinguishing characteristics through succeeding propagations by own-rooting, grafting and budding.

Locality where grown and observed: Richmond, Indiana.

*Flower*

Flowers borne: One to stem; on medium strong stems; on medium length stems.

Quantity of bloom: Abundant.

Continuity: Continuous during the summer.

Fragrance: Strong; tea.

Bud:

*Peduncle.*—Short; medium diameter; erect. Bark—entirely smooth. Color—Scheele's Green, Plate 860 (Wilson). Thorns—none. Prickles—few. Color—white. Hairs—few. Color—white.

*Before calyx breaks.*—Size—medium large. Form—ovoid; without foliaceous appendages on the surface of the bud; with slender, much-cut bristle-like foliaceous parts extending beyond the tip of the bud equal to one-fourth or more of its length. Color—Scheele's Green, Plate 860 (Wilson).

*As calyx breaks.*—Color—(outside of petal) Purple Madder, Plate 1028/3 (Wilson).

*As first petal opens.*—Size—medium large. Form—ovoid. Color: Outside—Rose Red, Plate 724/2 (Wilson); inside—Rose Red, Plate 724/2 (Wilson).

*Opening.*—Opens up well out-of-doors.

Bloom:

*Size when fully open.*—Large; 4 inches to 5 inches.

*Petalage.*—Double; from 35 to 40 petals arranged irregularly.

*Form.*—High centered at first, becoming open; petals being at first tightly rolled outward; becoming later at maturity loosely rolled outward.

Petals:

*Texture.*—Leathery. Inside—satiny; outside—shiny.

*Shape.*—Outside—obovate; flat apex. Intermediate—obovate; flat apex. Inner petals—obovate; apex flat; few with one notch.

This description of a newly opened flower was made from a rose grown out-of-doors in the month of August, at Richmond, Indiana:

*Color.*—Outside petal: outside surface—Rose Red, Plate 724 (Wilson); inside surface—Rose Red, Plate 724/1 (Wilson). Intermediate petal: outside surface—Rose Red, Plate 724/2 (Wilson); inside surface—Rose Red, Plate 724 (Wilson). Inner petal: outside surface—Rose Red, Plate 724/2 (Wilson); inside surface—Rose Red, Plate 724 (Wilson).

This description was made from a rose that was open for three days out-of-doors in the month of August, at Richmond, Indiana:

*Color.*—Outside petal: outside surface—Rose Red, Plate 724/1 (Wilson), overlaid with Tyrian Purple, Plate 727/3 (Wilson); inside surface—Rose Red, Plate 724/2 (Wilson). Intermediate petal: outside surface—Rose Red, Plate 724/1 (Wilson), overlaid with Tyrian Purple, Plate 727/3 (Wilson); inside surface—Rose Red, Plate 724/2 (Wilson). Inner petal: outside surface—Rose Red, Plate 724/1 (Wilson), overlaid with Tyrian Purple, Plate 727/3 (Wilson); inside surface—Rose Red, Plate 724/2 (Wilson).

*Behavior.*—Drop off cleanly; fading to Rose Red, Plate 724/3 (Wilson).

*Flower longevity.*—Cut roses grown out-of-doors kept at living-room temperatures—3 to 4 days in September. On bush in garden—4 to 5 days in September.

*General color effect.*—Newly opened flower—Rose Red, Plate 724 (Wilson). Three days open—Rose Red, Plate 724/3 (Wilson).

*Plant*

Foliage:

*Leaves.*—Compound of 5 to 7 leaflets; abundant; medium size; wrinkled; leathery.

*Leaflets.*—Shape—ovoid. Apex—mucronate. Base—round. Margin—simply serrate. Color: mature upper surface—near Parsley Green, Plate 00962 (Wilson); mature under surface—Spinach Green, Plate 0960/3 (Wilson); young upper surface—near Amaranth Red, Plate 43 (Koster); young under surface—near Amaranth Red, Plate 43 (Koster).

*Rachis.*—Heavy. Upper side—grooved; hairy. Under side—rounded (not grooved); prickly.

*Stipules.*—Medium length; medium width; with short points turning out at an angle of 45°.

Growth:

*Habit.*—Bush; much-branched.

*Growth.*—Vigorous.

*Canes.*—Large diameter.

*Main stems.*—Color—Spinach Green, Plate 0960 (Wilson). Thorns—few; short; hooked downward; with long, narrow base. Color—Van Dyck Brown, Plate 96 (Koster). Prickles—none. Hairs—none.

*Branches.*—Color—Spinach Green, Plate 0960/3 (Wilson). Thorns—few; short; hooked downward; with long, narrow base. Color—Pale Lilac Rose, Plate 34 (Koster) at base, shading to Artichoke Green, Plate 72 (Koster) toward tip. Prickles—none. Hairs—none.

*New shoots.*—Color—Scheele's Green, Plate 860/1 (Wilson). Thorns—very few; short; hooked downward; with long, narrow base. Color—near Amaranth Red, Plate 43 (Koster). Prickles—few. Color—Erythrite Red, Plate 0027 (Wilson). Hairs—none.

*Reproductive organs*

Stamens: Many; arranged irregularly about pistils.

Filaments: Vary in length from short to long; most with anthers. Color—Cardinal Red, Plate 822/3 (Wilson).

Anthers: Medium size; all open at once. Color—Persimmon Orange, Plate 710/3 (Wilson).

Pollen: Abundant. Color—Maize Yellow, Plate 607/2 (Wilson).

Pistils: Many.

Styles: Very uneven; medium length; heavy; bunched. Color—Cardinal Red, Plate 822/3 (Wilson).

Stigma: Color—white.

Ovaries: All usually encased in calyx.

Hips: None.

Sepals: Permanent; spear-shaped; curled. Color: Inside—near Spinach Green, Plate 0960/3 (Wilson); outside—Spinach Green, Plate 0960/2 (Wilson).

Seeds: None.

I claim:

A new and distinct variety of rose plant of the hybrid tea class, substantially as herein shown and described, characterized particularly as to novelty by the strong and compact bush habits of its growth, by the depth, intensity and luminosity of the Rose Red general color tonality of its flowers and the unusual uniformity of color through the different stages of its blooms from tight bud to fully open flower, by the unusual uniformity of color throughout each open bloom, by the resistance of its flowers to burn, fading and other effects of the sun, and by the unusually strong and distinctive tea fragrance of its flowers.

ROY L. BYRUM.

No references cited.